United States Patent [19]

Chakupurakal

[11] 4,318,770

[45] Mar. 9, 1982

[54] SURFACE ETCHING BEFORE ELECTRODING ZIRCONIA EXHAUST GAS OXYGEN SENSORS

[75] Inventor: Thomas Chakupurakal, St. Clair Shores, Mich.

[73] Assignee: General Motors Corporation, Detroit, Mich.

[21] Appl. No.: 177,561

[22] Filed: Aug. 13, 1980

[51] Int. Cl.$^3$ .............................................. C23F 1/00
[52] U.S. Cl. ................................... 156/637; 156/644; 156/667; 204/32 R; 204/195 S; 252/79.3; 427/309
[58] Field of Search ............... 156/644, 664, 667, 637, 156/638, 89, 663; 252/79.3; 204/195 S, 32 R; 427/309

[56] References Cited

U.S. PATENT DOCUMENTS

| | | | |
|---|---|---|---|
| 3,978,006 | 8/1976 | Topp et al. | 204/195 S |
| 4,021,326 | 5/1977 | Pollner et al. | 204/195 S |
| 4,135,012 | 1/1979 | Su | 156/667 X |
| 4,135,040 | 1/1979 | Thornton | 429/191 |
| 4,136,000 | 1/1979 | Davis et al. | 204/195 S |
| 4,138,881 | 2/1979 | Isenberg | 204/195 S |

*Primary Examiner*—William A. Powell
*Attorney, Agent, or Firm*—Robert J. Wallace

[57] ABSTRACT

A method of substantially increasing porosity and surface area on a zirconia body. The zirconia is etched with a mixture of concentrated hydrofluoric acid and concentrated sulfuric acid in a ratio effective to not only rapidly etch grain boundaries but to also rapidly pit individual zirconia grains. Concurrently the zirconia grains acquire a faceted or angular appearance. Etching is performed at 180°–220° C. for about 0.5–4 hours, along with ultrasonic agitation.

3 Claims, No Drawings

SURFACE ETCHING BEFORE ELECTRODING ZIRCONIA EXHAUST GAS OXYGEN SENSORS

FIELD OF THE INVENTION

This invention relates to surface preparation of zirconia exhaust gas sensor bodies before electroding. It more specifically relates to a process for etching such bodies before evaporating catalytic film electrodes thereon.

BACKGROUND OF THE INVENTION

Others have previously recognized that film electrodes on zirconia exhaust gas sensor bodies should be porous and adherent. Some electrodes formed by sputtering are inherently porous as deposited. Extremely high surface areas are obtained if the film electrodes are sputtered by the process described and claimed in U.S. Ser. No. 089,264, entitled "Exhaust Electrode Process for Exhaust Gas Oxygen Sensor", filed Oct. 29, 1979, now U.S. Pat. No. 4,244,798, in the names of T. J. Gold, F. L. Kennard, III, P. C. Kikuchi and R. V. Wilhelm, Jr. Evaporated film electrodes are not necessarily porous as formed. However, they can be made porous by appropriate heat treatment, as for example as described in U.S. Pat. No. 3,978,006 Topp et al.

Pretreating the zirconia substrate to enhance porosity and adhesion of a film electrode is described in U.S. Pat. No. 4,135,040 Thornton. Texturizing the zirconia surface should enhance electrode adhesion. Such a technique is presumably primarily applicable to film electrodes that are not inherently high in porosity and/or surface area as normally deposited. However, it may enhance characteristics of film electrodes that are inherently high in porosity and/or surface area as deposited. I have found an etching process and an etchant for zirconia that provides a high degree of zirconia texturing from both a macro and a micro standpoint. It is particularly effective in improving performance characteristics of evaporated catalytic film electrodes.

OBJECTS AND SUMMARY OF THE INVENTION

It is, therefore, an object of this invention to provide an improved etchant for zirconia for reception of film electrodes. Another object of this invention is to provide an improved process of preparing zirconia for receiving film electrodes, especially evaporated catalytic film electrodes.

These and other objects of the invention are obtained by applying a mixture of about 20–35% by volume concentrated hydrofluoric acid and the balance substantially concentrated sulfuric acid to a zirconia surface for about 0.5–4 hours. During most, if not all of the etching the etchant is maintained at a temperature of about 180°–260° C. and is continuously stirred. During etching, or at least during a final stage in the etching, the zirconia surface is subjected to ultrasonic agitation. If the ultrasonic agitation is performed after etching is substantially completed, the etchant temperature can be allowed to drop below about 180° C. during the ultrasonic agitation. The zirconia surface is then rinsed and dried. It is then heated to an elevated temperature, preferably about 1000° C., for one hour. Thereafter, the zirconia body can be placed in a vacuum chamber, degassed and electroded. I prefer to do the electroding by the evaporation technique described and claimed in my copending U.S. patent application Ser. No. 177,617, entitled "Evaporated Electrodes for Zirconia Exhaust Gas Oxygen Sensors", which is filed concurrently herewith and is assigned to the assignee of this invention.

DESCRIPTION OF THE PREFERRED EMBODIMENTS

In a specific example, my process was practiced on hollow tapered polycrystalline zirconia, i.e. zirconium dioxide, thimbles of the particular shape and dimensions described in U.S. patent application Ser. No. 080,449, entitled "Reference Electrode Printing Process and Mask for Exhaust Gas Oxygen Sensor", which was filed by John Trevorrow on Oct. 1, 1979, now U.S. Pat. No. 4,264,647. As usual the zirconia is partially or completely stabilized in its cubic crystalline form. The tapered cone-like portion of the thimble is about 3 cm long that extends from a thickened flange or butt portion. Immediately below the flange, the outer diameter of the cone is about 0.6 cm. Such thimbles are also shown in U.S. Pat. No. 3,844,920, R. R. Burgett and B. W. Holleboom.

If desired one may choose to degrease the zirconia thimbles in a chlorinated organic solvent before etching in accordance with this invention. If so, trichloroethylene, freon, or the like, can be used. Then, about 6–8 of the tapered hollow zirconia thimbles such as described in the aforementioned U.S. Ser. No. 080,449 can be placed on a horizontal open polytetrafluoroethylene support spaced about 1–2 cm above the bottom of a cylindrical 500 ml polytetrafluoroethylene beaker. The beaker contains about 250 ml of an approximately 1:3 mixture, by volume, of concentrated hydrofluoric acid to concentrated sulfuric acid, respectively. The quantity of acid covers all of the zirconia thimbles by more than about 1 cm.

Before the zirconia thimbles are placed in the beaker, the beaker was placed on a hot plate and the 1:3 acid mixture heated to a temperature of about 220° C. The heater control is then adjusted to maintain the acid mixture at that temperature. The hot plate should also have a capability for magnetically stirring the acid mixture to provide a safer means for continuous stirring of the etchant during etching. For the magnetic stirring, a plastic encapsulated iron rod is disposed in the beaker beneath the thimble support. The magnetic stirring can be set for about 1–5 revolutions per second, and is continuously performed during etching while the beaker is on the hot plate.

The thimbles begin to etch when immersed in the beaker. As etching proceeds, the etchant gradually increases in viscosity, apparently due to complexes which the zirconium ions form. The rate of this increase depends on factors such as the etching rate and the ratio of the zirconia surface area being etched to the volume of the acid mixture used. In this example, after about 2 hours, viscosity of the etchant may increase to such an extent that it can no longer be effectively stirred magnetically. In such event, I prefer to thin the etchant by adding about 50 ml more of fresh 1:3 etchant, and then continue etching. Preferably the fresh etchant is preheated to 220° before it is added to the beaker. If about 50 ml more does not thin the etchant enough to allow good etching, then more fresh acid mixture should be added. The quantity of extra acid needed, if needed at all, can vary. In any event, etching is then continued for another two hours, for a total of about four hours.

The zirconia thimbles are subjected to ultrasonic agitation for at least about one hour during the etching. This generally can be done after etching is well underway, and even after substantial etching has been completed. I do not have a single apparatus that provides heating, magnetic stirring, and ultrasonic agitation. Instead I use a hot plate that has adjustable heating and magnetic stirring. Ultrasonic agitation is done in a separate ultrasonic agitator of the water bath type. It includes means for maintaining the water bath at about 100° C.

As described above, the zirconia thimbles are etched on the hot plate with continuous magnetic stirring. The temperature is maintained at about 180°–260° C. for about 0.5–4.0 hours. After etching preferably at 220° C. for about four hours on a hot plate, I transfer the beaker to the ultrasonic agitator water bath. The water bath of the ultrasonic agitator is preheated to 100° C. at the time of transfer and the beaker is transferred while still at the desired etching temperature, as for example 220° C. Ultrasonic agitation is immediately started and continued for an hour, regardless as to the temperature or length of time of the etching preceding it.

I believe that the ultrasonic agitation removes loose debris from the surface of the thimbles and permits a fuller detail of etch facets to be developed in the etch pits in the zirconia grains and on the grain surfaces along grain boundaries. I have shown that satisfactory results are obtained with only an hour of ultrasonic agitation while the etchant is cooling from 180°–220° C. toward the 100° C. temperature of the ultrasonic agitator water bath. However, I believe that the same or even better results would be available with longer ultrasonic agitation, ultrasonic agitation earlier during etching, or even continuously during etching, if the desired etching temperature could also be maintained.

After the ultrasonic agitation, the zirconia thimbles are removed from the beaker, rinsed in deionized water, rinsed in acetone, rinsed again in deionized water, and then dried. They are then heated in air to a temperature of about 1000° C. and held there for about one hour. The firing at 1000° C. significantly enhances the effect of the aforementioned chemical etching. I believe it removes residual acids, salts, and the like that are not removed from the etched surface by the aforementioned rinsing. One hour at 1000° C. will remove them. Hence, more severe treatments, i.e. of higher temperature and/or longer time, are unnecessary. It may even be undesirable to heat the zirconia above about 1250° C. I presume that a temperature of at least about 800° C. should be used but longer soak times may be needed when using this lower temperature. The rate of heating and cooling during this firing is not material to this invention. By way of example, but not limitation, the thimbles can be placed in a furnace that is at room temperature. The furnace is then heated to 1000° C. and held there for one hour. Heating is then discontinued and the furnace allowed to cool to a temperature below about 200°–300° C. It is then opened to ambient room conditions and the thimbles removed. If desired, the furnace can be allowed to cool to room temperature before it is opened. The thimbles are ready for electroding when removed from the furnace. Electrodes are then preferably evaporated onto the thus treated zirconia surface as described in my aforementioned concurrently filed U.S. patent application Ser. No. 177,617. However, film electrodes can also be deposited on the zirconia bodies by sputtering using a process such as described and claimed in the aforementioned U.S. Ser. No. 089,264.

Any number of zirconia bodies can be etched at the same time in a common container. On the other hand, it should be recognized that the etching of this invention vigorously attacks the zirconia, and for this reason the container should contain suitable space and means above the surface of the etchant to contain the vigorous reaction. Still further, the reaction is highly exothermic. It produces a vigorous boiling that evolves acid fumes. I prefer to conduct the etching in a hood with a funnel nested over the beaker to condense acid vapors and return them to the beaker during etching. However, it is recognized that one may prefer to isolate and/or recycle these fumes in other ways.

As hereinbefore mentioned, by etchant is a mixture of concentrated hydrofluoric acid (48% by weight HF) and concentrated sulfuric acid (98% by weight $H_2SO_4$). I prefer that my acid consist of about 20–35% by volume concentrated hydrofluoric acid and the balance, i.e. 80–65% by volume, concentrated sulfuric acid. The hydrofluoric acid adds greater depth of etching into the zirconia surface. It apparently attacks glassy phases of the polycrystalline zirconia that are present along grain boundaries. It also seems to help in providing additional etch pits on the individual zirconia grains. In addition, the hydrofluoric acid makes the etching more vigorous, which adds etching speed to the etchant. In fact, if less than about 20% by volume of concentrated hydrofluoric acid is present, comparatively little etching occurs, even at 260° C. If 40% or more by volume concentrated hydrofluoric acid is used, the reaction of the etchant on the zirconia is extremely violent and the etch pattern does not retain the sharply faceted definition that is desired. Zirconia grains are not merely pitted. They are reduced in size, and perhaps even etched completely away. Etching at grain boundaries does not appear to have as much depth, perhaps because whole layers of zirconia grains etch away before grain boundaries can etch very deeply. With about 20–35% by volume hydrofluoric acid in the mixture, there appears to be an adequate balance between reaction rate and pattern definition in the resultant substrate. Within this range, the grain boundaries widen, presumably along the crystalline defect structures, such as dislocations and stacking faults. This opens comparatively wide and deep cracks along the boundaries between individual zirconia grains. I refer to this as a macro-etching effect. Concurrently, the grains themselves are uniquely etched with triangular, hexagonal, and square etch pits, and the zirconia grains acquire an angular or faceted surface. I refer to the pitting and faceting as a micro-etching effect.

In order to obtain the highly desirable type of etch described in the preceding paragraph, the etchant should be maintained at a temperature of approximately 180°–260° C. At as low as about 21° C. virtually no etching action occurs. With increasing temperature, the rate of etching increases. On the other hand, the character of the surface produced by lower temperature etching is not particularly desirable. It does not exhibit the angular or faceted appearance described in the preceding paragragh until an etching temperature of about 180° C. is used. With increasing temperature above about 260° C. the etched surface tends to lose the angular or faceted definition and/or etch depth. This is perhaps because the etching is more rapid, and tends to etch away whole zirconia grains rather than merely etch pits in them.

In general, at least about 0.5 hour is necessary in order to see any appreciable porosity develop in the etched surface. I prefer to etch about 2-4 hours. Three hours may be an adequate etching time but in most instances I prefer to etch for an additional hour to insure that a satisfactory surface pattern has been developed. It does not appear that extending the etch time is detrimental. It simply does not provide any additional benefits. As previously mentioned, I complete the etching by an additional hour of ultrasonic agitation while the etchant is cooling from the preferred etching temperature towards 100° C. I expect that about 0.5 hour agitation would be adequate and that periods above one hour would not be deleterious, just unnecessary. It is doubtful that the etchant would actually be stabilized at a temperature of 100° C. with only about 0.5 hour immersion in the water bath. In fact I presume that it would not even be stabilized at 100° C. after one hour.

It was previously mentioned that an additional quantity of fresh etchant was used to thin the etchant as etchant viscosity increased during etching. It may not be necessary to have a fresh quantity of etchant, if fewer thimbles were etched in the same acid volume, or if a larger acid volume were used for the same number of thimbles. In general, I would expect that the higher the volume of etchant to the area of zirconia surface being etched, the less likely the etchant will need replenishment, or thinning, as etching proceeds. Also if a very high ratio of acid volume to zirconia surface area is used, the importance of thorough stirring, i.e. magnetic stirring, may be reduced.

After the thimbles are removed from the etchant, it is important to remove any residual traces of the concentrated acids or the like that remain on the thimble surfaces. For this reason the thimbles are thoroughly rinsed with water and acetone, as previously described. Rinsing with acetone removes organics that may be present. Heating the etched zirconia thimbles for about one hour at about 800°-1250° C. completes cleanup of the thimble surfaces by volatilizing residual surface contamination that is not removed by rinsing. Most adherent and fastest responding film electrodes have been obtained if the zirconias were so heat treated after etching and before electroding.

The etching provided by this invention apparently drastically opens up the zirconia surface area, to provide a resultant surface area approximately 5-10 times, often 7 times, larger than the original surface area. This not only provides an enhanced basis for obtaining high surface area film electrodes on the zirconia but also improved electrode adherence. In addition, it appears that zirconia bodies etched in accordance with this invention are stronger. I believe that this is due to a removal of zirconia surface defects where cracks can start. Analogously, I believe that propagation of cracks, once started, is inhibited because cracks would more likely propagate along defects. However, the defects have been etched away to significant depth of the surface. Tests indicate that evaporated electrodes on such etched surfaces are considerably more porous and have a much higher surface area.

The acids used in my etchant are preferably concentrated. By concentrated I mean the most concentrated form which is generally commercially available. By this I mean hydrofluoric acid containing 48% by weight HF and sulfuric acid containing 98% by weight $H_2SO_4$. I have added up to 6% by volume water to the acid mixture but found that the etch rate slows and the etch quality degrades. Presumably etch rate can be accelerated by heating the mixture to permit a greater amount of tolerance for water. However, I prefer to use the etchant at lower temperatures, and for this reason prefer to use the undiluted acids. As to the inclusion of other acids and salts to my preferred 1:3 acid mixture, they would not be objectionable so long as they do not materially degrade the basic and novel characteristics of my preferred 1:3 acid composition.

The embodiments of the invention in which an exclusive property or privilege is claimed are defined as follows:

1. A method of substantially increasing porosity on a polycrystalline zirconia surface comprising etching the zirconia surface with an etchant consisting essentially of concentrated hydrofluoric acid and concentrated sulfuric acid in a ratio effective to not only rapidly etch grain boundaries but to also rapidly etch individual zirconia grains and thereby provide relatively large pores between the grains and small pores on the grains.

2. A method of substantially increasing porosity on a zirconia surface comprising etching the surface with a mixture consisting essentially of about 20-35% by volume concentrated hydrofluoric acid and the balance concentrated sulfuric acid for at least about 0.5 hour at about 180°-220° C.

3. The method of preparing a surface on a zirconia solid electrolyte body for an oxygen sensor to receive an evaporated metal electrode comprising the steps of:

heating an acid mixture to a temperature of about 180°-220° C., said acid mixture containing about 1 part concentrated hydrofluoric acid, about 3 parts concentrated sulfuric acid and up to about ¼ part water;

immersing the zirconia solid electrolyte body in the etchant;

maintaining the immersion at said temperature for about 0.5-4 hours while simultaneously stirring the etchant;

ultrasonically agitating the etchant for at least about 0.5 hour while said body is immersed therein;

removing the body from the mixture and rinsing it;

drying the body; and heating the body to a temperature of at least about 800° C. for at least about an hour to volatilize residual surface contamination.

* * * * *